(12) United States Patent
Kashyap

(10) Patent No.: US 7,156,870 B2
(45) Date of Patent: Jan. 2, 2007

(54) FLOW MAINTAINING STENT DELIVERY SYSTEM

(76) Inventor: Ravindra L. Kashyap, 225 79th St., Brooklyn, NY (US) 11209

( * ) Notice: Subject to any disclaimer, the term of this patent is extended or adjusted under 35 U.S.C. 154(b) by 544 days.

(21) Appl. No.: 10/356,968

(22) Filed: Feb. 3, 2003

(65) Prior Publication Data
US 2003/0220680 A1    Nov. 27, 2003

Related U.S. Application Data

(60) Provisional application No. 60/365,504, filed on Mar. 19, 2002, provisional application No. 60/354,188, filed on Feb. 4, 2002.

(51) Int. Cl.
*A61F 2/84* (2006.01)
*A61F 2/06* (2006.01)
(52) U.S. Cl. .................................... 623/1.11
(58) Field of Classification Search ............ 623/1.11, 623/1.12; 606/198, 108
See application file for complete search history.

(56) References Cited

U.S. PATENT DOCUMENTS 6,468,298 B1 * 10/2002 Pelton ...................... 623/1.11

* cited by examiner

*Primary Examiner*—Anhtuan T. Nguyen
*Assistant Examiner*—Elizabeth Houston
(74) *Attorney, Agent, or Firm*—Carter DeLuca, Farrell & Schmidt LLP

(57) ABSTRACT

The present invention is directed to a Flow Maintaining Stent Delivery System, FMSDS, which can be used in many cardiovascular and surgical procedures, especially for placing stents into patients having stenosed and occluded arteries and other vascular lumens. It can also be used as an examination tool for the vascular surgical operations and to examine small orifice internal or external to the body. Most important, the advantage of the present stent delivery system is that it allows antegrade downstream blood flow to be maximally maintained during stenting procedures, angioplasty procedures or in any other vascular surgical operations that can use this system. The present invention also allows for uniform placement of the stent onto the artery.

16 Claims, 3 Drawing Sheets

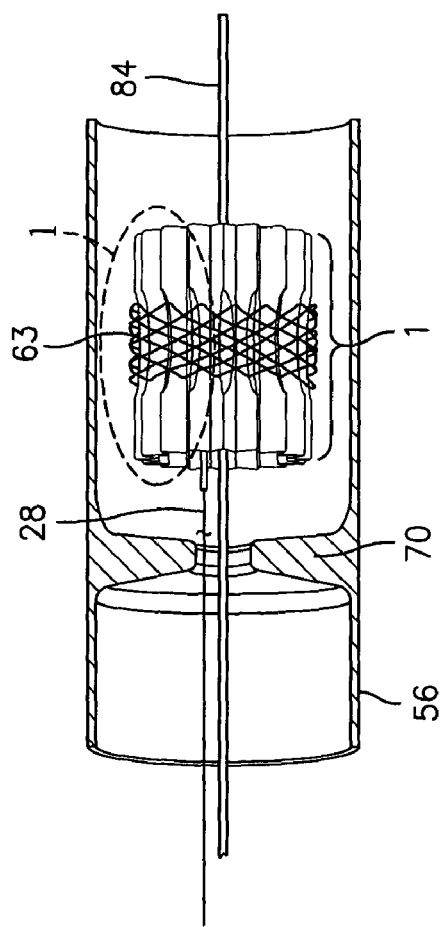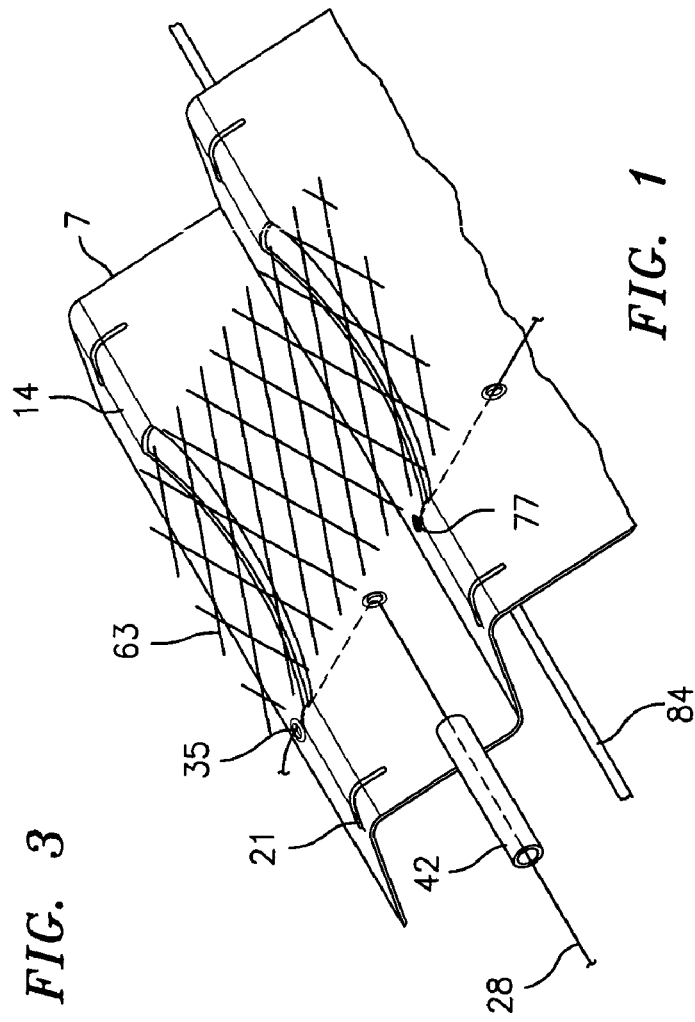

FLOW MAINTAINING STENT DELIVERY SYSTEM

PRIORITY

This patent application claims priority to a United States Provisional Application filed on Mar. 19, 2002 and assigned U.S. Provisional Application Ser. No. 60/365,504 and to a United States Provisional Application filed on Feb. 4, 2002 and assigned U.S. Provisional Application Ser. No. 60/354,188, the contents of both applications are incorporated herein by reference.

BACKGROUND OF THE INVENTION

1. Field of the Invention

The present invention relates to a medical/surgical angioplasty and stent delivery system, and also its multi-purpose use as a small retractor to virtually keep open any small orifice of the body.

2. Description of the Related Art

Many balloon stent delivery systems occlude blood flow during stenting operations. For laminar flow the equation of flow in an artery is: $Q$ (Flow)$=\Delta P/R_f=\Delta P/8\eta l/\pi R^4=\pi R^4 \Delta P/8\eta l$ (where $\Delta P$ is change in pressure; $R_f$ is resistance; $\eta$ is viscosity of fluid like blood; $l$ is length of the artery; and $R$ is radius of the artery). Most important, in the above equation for flow, $Q$, derived from physical principles is proportional to $R^4$ ($R$ being the radius of an artery). Thus any incremental decrease or increase in the radial length $R$ of the artery has tremendous effect on blood flow $Q$. So, stent delivery systems that allow for an incremental decrease in the radial lumen length of an artery will substantially impede blood flow. In particular the interruption of blood flow to the heart is so critical to patients during angioplasty and stenting operations, that the system of using balloons as delivery system may not be efficient.

In fact during angioplasty and stenting procedures, cardiologists have only seconds to inflate then deflate the balloon and take it out. However, the current embodiment of the stent delivery system allows for the maximal maintenance of downstream antegrade blood flow while the stent is being placed and/or when angioplasty is performed. This improvement is considerably important to patients and offers cardiologists an efficient way to deliver stents and do angioplasty without worrying about inflating and deflating the balloon quickly in matter of seconds. The balloon angioplasty and stent delivery devices offer uniformity and better custom fit of stents, which may be lacking in self-deploying stents. And this advantage of uniformity and better custom fit is preserved in this current embodiment. The current invention can be made entirely of smooth metal or flexible plastic plates that conveniently allows for complete sterilization, so it can be used again and again. Or else the FMSDS can be made entirely from plastics, making it disposable.

SUMMARY OF THE INVENTION

The present invention is directed to a flow maintaining stent delivery system, FMSDS, which has multiple uses. The stent delivery system can be used to introduce a stent within a blood vessel, and for other surgical procedures, such as to perform angioplasty or to be used as a retractor during a surgical operation. A preferred embodiment is made from smooth metal plates or smooth flexible plastic plates, springs, hinges, and strings/wires; and which are able to withstand high temperatures. Essentially, the FMSDS can go from a very small diameter cylindrical structure to a very large diameter. Any small opening can be enlarged in this manner. It can produce adequate force to keep any surgical orifice, artery, or vascular structure open steadily and in a stable manner without rupture of the vessel. More importantly, as mentioned above, FMSDS can be used to place a stent in cases of coronary artery artherosclerosed plaque obstruction or for peripheral vascular diseases. After use FMSDS can be made to collapse and contract easily and completely, and taken out of the body within seconds.

FMSDS operates on the principle that the springs exert adequate force to keep the apparatus fully expanded and opened into a bigger diameter hollow cylindrical structure. Counteracting the effect of the springs are the string/wire that prevents the embodiment from opening and expanding. But when the string/wire is slowly released and unwound the embodiment opens completely into a larger diameter structure from an initial smaller diameter hollow cylindrical structure, and when the string/wire is wound up the apparatus collapses and contracts into a smaller diameter configuration from a larger diameter structure. Note that the cylindrical configuration depicted in this embodiment is just one of many different types of configurations, sizes, and shapes that can be constructed based on the same thematic design.

Initially, the non-expanded stent stably rests within the smooth elliptical groove of FMSDS, and the stent will expand in circumference with the expanding apparatus. Eventually the stent will be pressed against the arterial wall retracting the artherosclerotic plaque of the coronary artery onto the artery itself. In this current embodiment the advantage is that the stent is placed uniformly onto the arterial wall with a perfect custom fit, just as is the case with the balloon delivery system, however, this may not be the case with self-deploying stents. But the most significant advantage of this embodiment over other stent delivery system is that FMSDS allows the downstream antegrade blood flow to be maximally maintained throughout stenting or angioplasty procedure. At no time is the blood flow obstructed or hindered during the stenting or angioplasty operation. Since flow $Q$ is proportional to $R^4$ (where $R$ is the radius of the artery), then any incremental decrease in the lumen diameter of an artery as with a balloon inflating devices will cause tremendous decrease in blood flow. Decreased blood flow in coronary artery poses great danger to patients, which this current embodiment circumvents. Furthermore, this embodiment of the FMSDS is heparinized; it has no sharp edges, with all areas of FMSDS made smooth, and flexible to prevent coagulation and lacerations of the artery that may occur during the stenting or angioplasty procedure. And if the FMSDS is made from metal then it can be sterilized and used again and again, or it can be made completely from non-allergic disposable plastics.

BRIEF DESCRIPTION OF THE DRAWING FIGURES

The invention will be described in greater detail with reference to the accompanying drawings in which like elements bear like reference numerals, and wherein:

FIG. 1 is a schematic showing the assembly of the metal plates or flexible plastic plates, hinges, springs, tubes and string/wire into a cylindrical configuration of the present invention;

FIG. 3 is a schematic showing the contracted form of the embodiment of the present invention;

DETAILED DESCRIPTION OF THE PREFERRED EMBODIMENTS

Figure 2:
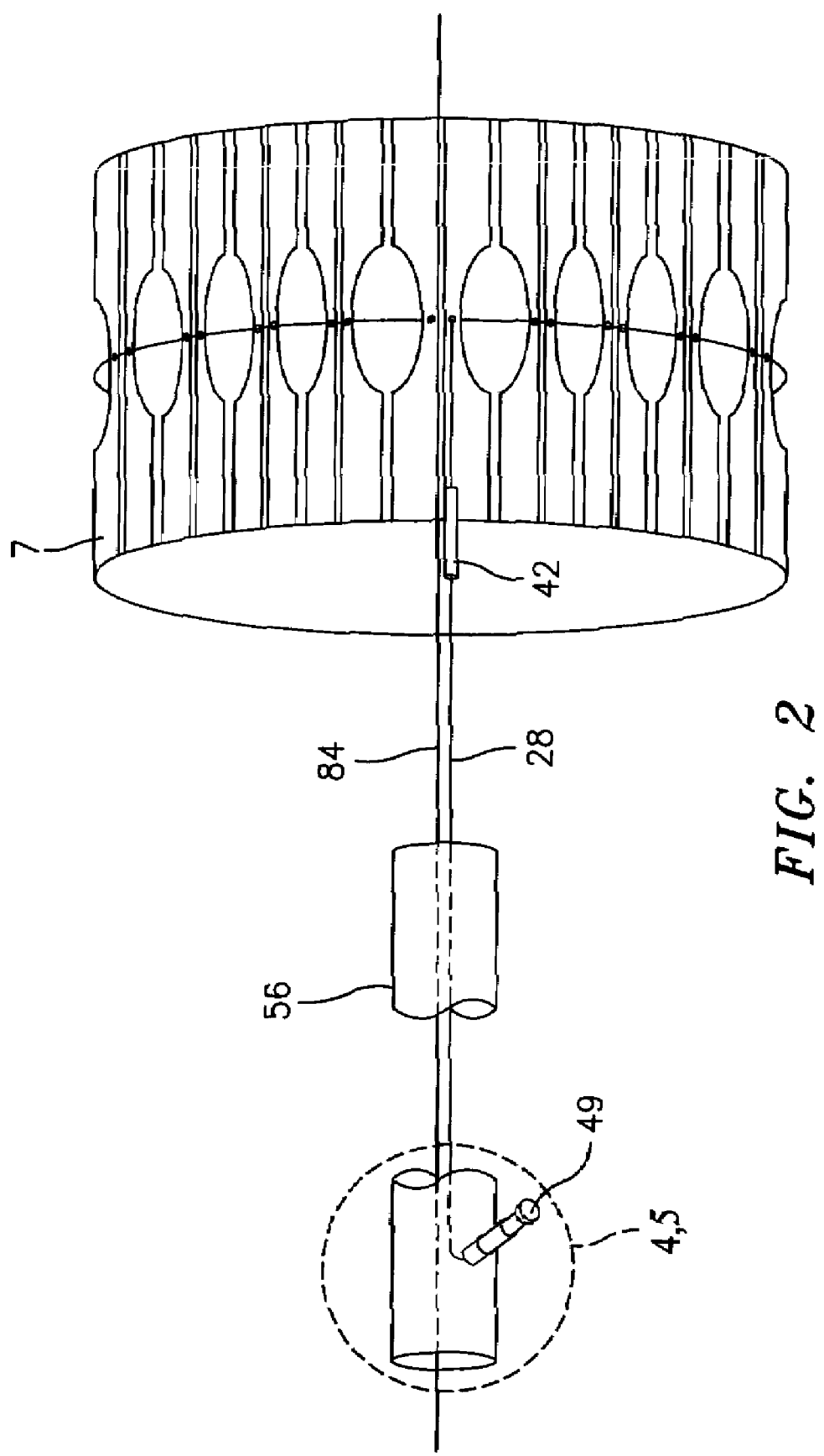
FIG. 2 is a schematic showing the expanded form of the embodiment of the present invention.

This instrument is primarily designed to deliver stents during stenting operation for coronary artery disease obstruction and to be used for angioplasty purposes. Thin metal plates, or flexible transparent (bioluminescent or x-ray luminescent) plastic plates 7 are adjacent to each other; see FIG. 1. The plates 7 have elliptical cuts at their center and form an angle with respect to each other as shown by reference numeral 14; see FIG. 1. These elliptical cuts form a grove on the embodiment where the stent 63 sits and do not allow the stent 63 to slip away from the stent delivery system during stent placement procedure inside the coronary artery. Between the plates there are small hidden springs 21 that articulate between adjacent plates 7, see FIG. 1. The springs 21 are structured such that they provides adequate force to cause the angle between adjacent plates 7 to approach approximately 180 degrees.

The springs 21 are configured to maintain a specific configuration of the apparatus (a cylindrical one as presented in this embodiment) by guiding the motion of the plates 7. (Note that instead of the springs and hinges in between the plates one could make this junctional area out of a contiguous "springing" material that will function just as well as the springs and hinges.) At the middle of the plates 7, holes 35 are provided which act as bearings. In one end, the string/wire 28 permanently attaches onto the last plate 7, called the anchor point for the string/wire, 77, see FIG. 1. The string/wire 28 then goes through the bearing holes 35 of all the plates 7, and exits on the first plate and then it goes through the very small hard protruding tube 42, see FIG. 2 and FIG. 1, respectively.

The bearing holes 35 prevent the string/wire 28 from cutting the plates 7 when the tension is very high on the string/wire 28. Note that the above created and constructed embodiment is called FMSDS 1 and can be made to sit inside another bigger diameter plastic tube called the introducing catheter 56 from which it can be ejected, FIG. 2 and FIG. 3. After exiting the tube 42, the string/wire 28, will travel inside the introducing catheter 56, going through the string/wire restricted holes 98, and exit from a small hole of the introducing catheter and permanently attach itself to the screw knob 49. The screw knob 49 acts as controls for FMSDS 1 and for stent deployment through its action on the string/wire 28.

The screw knob 49 has threads to create enough friction, which will not allow the string/wire 28 to unravel or lose its tensile strength unless someone operates the screw knob 49. The tenacious string/wire 28 has two functions, first, it is used to push (and subsequently pull) the contracted FMSDS 1 apparatus (see FIG. 3 and FIG. 2) over the guide wire 84 to be placed at the coronary artery's plaque stenosed area and, second, the string/wire 28 is used to inflate FMSDS 1 for stent deployment. (Note that the introducing catheter 56 may have plastic mounds 70 which may or may not be necessary to make the FMSDS 1 be stationed in a stable manner inside the introducing catheter, as shown in FIG. 3.)

Figure 4:
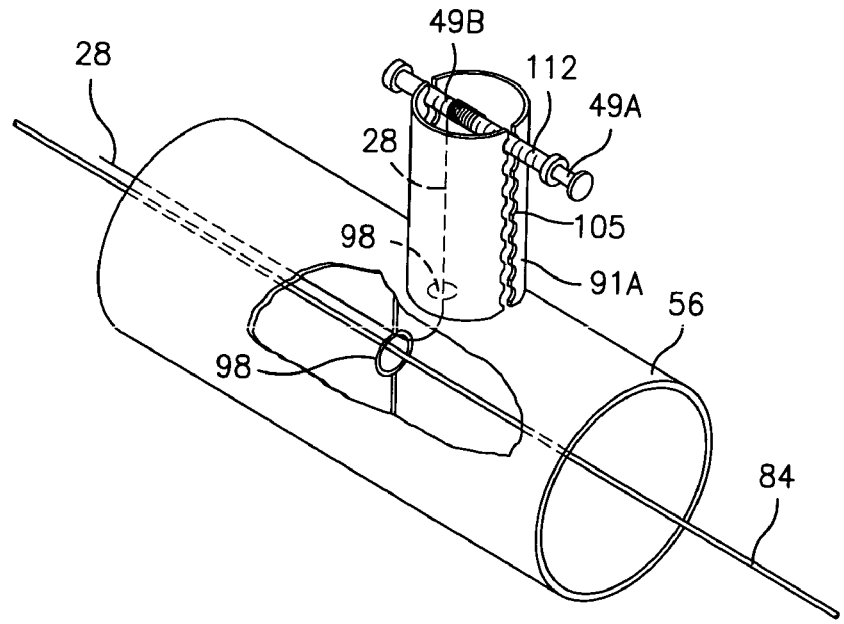
FIG. 4 is a schematic showing the "syringe type" controls for FMSDS.

Now, in the following there are two designs mentioned that act as controls for the FMSDS 1:

1. One way for the controls of the FMSDS 1 is as shown in FIG. 4. In this configuration, the screw knob holder 91A has in it screw knob holder holes 105, see FIG. 4. The screw knob 49A shaft extends out from one side of the screw knob holder holes 105 and exits out by traversing another set of screw knob holder holes 105 on the other side of 91A, see FIG. 4. On the distal end of the screw knob 49A shaft outside the screw knob holder 91A there is a permanently attached large diameter knob that prevents the screw knob 49A from disassembly and sliding off the screw knob holder holes 105 and the screw knob holder 91A itself, see FIG. 4. In the middle of the screw knob 49A shaft there are screw knob threads 49B, which wrap the string/wire 28 onto itself, see FIG. 4. The screw knob holder holes 105 are corrugated such that they allows the screw knob 49A shaft to vertically slide in between the holes 105 passing by the constricted areas present between the screw knob holes as shown in FIG. 4. As the screw knob 49A shaft goes from one screw knob hole 105 to the next in a downward vertical direction, it causes the string/wire 28 to move in an axial direction hence pushing the FMSDS 1 out of the introducing catheter 56 to be placed inside the coronary artery lumen where the plaque deposit obstruction is located. To inflate the FMSDS 1 the screw knob 49A must be rotated to unwind the string/wire 28, from the screw knob threads 49B, thereby releasing the string/wire 28 tension on the FMSDS 1; and automatically the springs 21 exert its centrifugal force to expand the FMSDS 1, see FIG. 2. With the expanding FMSDS 1, the stent expands and achieves a uniform and an individually better custom fit onto the arterial wall. At this point note that the FMSDS 1 delivery system need not be removed immediately, because the downstream antegrade blood flow inside the coronary artery is maximally maintained, which in contrast to conventional balloon stent delivery systems. After a stent or angioplasty procedure, the screw knob 49A is rotated such that the string/wire 28 is wound up onto the screw knob threads 49B creating back the original tension on the string/wire 28 which overcomes the centrifugal forces exerted by the springs 21 eventually to contract and deflate the FMSDS 1. Then the screw knob 49A shaft can be moved upward direction from one screw knob hole 105 to the next causing the reverse axial motion of the string/wire 28, see FIG. 4. This eventually leads to the drawing in of the contracted FMSDS 1 apparatus into the introducing catheter 56, see FIG. 3. To control the vertical motion of the screw knob 49A shaft, a screw knob lock 112 which is a hard cylindrical cover casing structure resides over the screw knob 49A shaft outside of the screw knob holder 91A as shown in FIG. 4. At the distal end of the screw knob lock 112 there are few threads on its outside surface that will articulate with the few threads on the screw knob holes 105 inside surface, see FIG. 4. When the screw knob lock 112 is rotated and screwed into the screw knob holder holes 105, prohibition of rotational and vertical motion of the screw knob 49A shaft is achieved. So, the screw knob lock 112 allows for the arrest of the axial motion of the string/wire 28 and fixes the FMSDS 1 at any given position along the axial length of the embodiment. One must release the screw knob lock 112 and pull it back in order for the screw knob 49A shaft to move up and down the screw knob holes 105. Note the presence of the string/wire restricted holes 98, which guide the string/wire 28 along its axial motion line inside the embodiment.

Figure 5:
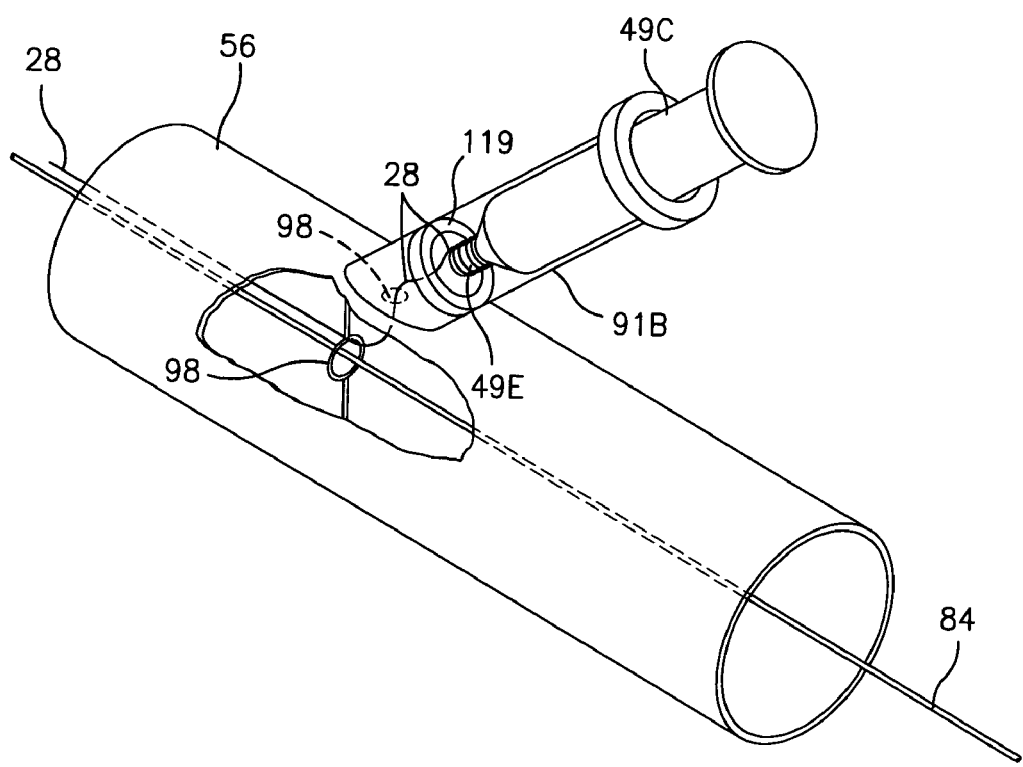
FIG. 5 is a schematic showing the "vertical type" controls for FMSDS.

2. Alternatively, as shown in FIG. 5, a syringe type screw knob 49C can be constructed, which resides inside a screw knob holder 91B that may be filled with contrast material or saline or the same fluid which is in the introducing catheter 56 or it could remain empty, see FIG. 5. The screw knob syringe plunger 49C will be slowly pushed through the screw knob syringe holder 91B pushing (the fluids, if it is present) and causing the axial motion of the string/wire 28 and subsequently the FMSDS 1. (Note that the hard plastic screw knob syringe plunger stopper mound 119 will not let the screw knob syringe plunger 49C go beyond a certain point.) By doing so the FMSDS 1 will be placed under the artherosclerosed obstructing plaque of the coronary artery. Then a twisting and unscrewing rotational motion of the screw knob syringe plunger 49C will cause its miniature threads 49E to unwind the string/wire 28 reducing its tension and automatically triggering the springs 21 to exert its centrifugal force whereby the FMSDS 1 apparatus completely opens and inflates, see FIG. 2. An expanding FMSDS 1 apparatus will expand the stent onto the obstructive plaque with a uniform and individually better custom fit onto the coronary artery. As mentioned before, at this point note that the FMSDS 1 delivery system need not be removed immediately within seconds because downstream antegrade blood flow inside the coronary artery is maximally maintained, and again, this unfortunately does not happen with the balloon stent delivery systems. Once the stent is in place, the screw knob syringe plunger 49C will be twisted and rotated in such a way that it winds up the string/wire 28, increasing its tension to overcome the centrifugal forces exerted by the springs 21 causing the FMSDS 1 to contract and deflate into a smaller diameter configuration from a larger diameter configuration, see FIG. 3. A contracted FMSDS 1 can be pulled into the introducing catheter 56 by slowly pulling the screw knob syringe plunger 49C upward, see FIG. 3 and FIG. 5. Note the presence of the string/wire restricted holes 98, helps guide the motion of string/wire 28 along its axial line inside this embodiment.

Since flow Q is proportional to $R^4$ (where R is the radius of the artery), any incremental change in the radial length of a given artery will make tremendous difference in flow. Flow is critical to the stenting operation as any obstruction or decrease in radial length will lead to fatal cardiac problems such as ventricular fibrillation, ventricular arrhythmia or ventricular tachycardia etc. Hence, the advantage of FMSDS 1 delivery system unlike the balloon systems is that this delivery system allows the maintenance of maximum possible downstream antegrade blood flow by least possible non-obstruction in the radial length of the coronary artery throughout the stenting or angioplasty process. More over the FMSDS 1 system provides a uniform as well as individualized better custom fit of the stent inside coronary artery walls, just as good as the balloon devices do, but this may not happen with the self-deploying stent delivery systems. Also this delivery system can be cleaned and sterilized and can be used again if it is made from smooth flexible metallic plates. However, if FMSDS 1 is made from non-allergic plastic then it can be disposed.

The FMSDS 1 must be heparinized, made with complete smooth edges that have great flexibility so as to not cause any coagulations, lacerations and injury inside the coronary arteries. Appropriate markers and bioluminescent dye and materials can be applied to the FMSDS 1 for aiding in positioning the FMSDS 1 inside the heart or other part of the body when doing stenting and angioplasty procedures. Finally, note that many different shapes and sizes and lengths can be designed on this particular theme of the stent delivery system.

What is claimed is:

1. A stent delivery system comprising:
   a plate mechanism having a plurality of plates configured for forming a circular configuration, a wire in operative communication with the plurality of plates for controlling the formation of the circular configuration, each of the plurality of plates defining at least one opening for passage there through of the wire wherein at least one of the plurality of plates rotates in a clockwise direction and at least one adjacent plate of the at least one of the plurality of plates rotates in a counter-clockwise direction during formation of the circular configuration;
   a spring mechanism configured to adjust the tightness of the wire for maintaining the plurality of plates in one of a plurality of configurations including the circular configuration;
   a stent configured and dimensioned for being supported by a portion of each of the plurality of plates; and
   an control mechanism for controlling the spring mechanism to position the plurality of plates in one of the plurality of configurations.

2. The stent delivery system according to claim 1, wherein the control mechanism enables the stent to be positioned against a wall of a body lumen while maintaining flow through the body lumen.

3. The stent delivery system according to claim 1, further comprising a catheter in operable communication with the plate mechanism for guiding the plate mechanism within a body lumen.

4. The stent delivery system according to claim 1, wherein the control mechanism includes at least one control knob for controlling the spring mechanism.

5. The stent delivery system according to claim 4, wherein the at least one control knob includes locking structure for locking the at least one control knob in one of a plurality of positions.

6. The stent delivery system according to claim 5, wherein movement of the at least one control knob from a first to a second position of the plurality of positions controls the tightness of the wire.

7. The stent delivery system according to claim 4, wherein the at least one control knob comprises a syringe mechanism.

8. The stent delivery system according to claim 7, wherein the syringe mechanism is in operative communication with the wire, and wherein motion of the syringe mechanism controls the tightness of the wire.

9. A method for delivering a stent within a body lumen comprising:
   providing a plate mechanism having a plurality of plates configured for forming a circular configuration, each of the plurality of plates defining at least one opening for passages there through of a wire for controlling the formation of the circular configuration upon movement of the wire; wherein at least one of the plurality of plates rotates in a clockwise direction and at least one adjacent plate of the at least one of the plurality of plates rotates in a counter-clockwise direction during formation of the circular configuration;

providing a spring mechanism configured to adjust the tightness of the wire traversing at least one of the plurality of plates for maintaining the plurality of plates in one of a plurality of configurations including the circular configuration;

supporting the stent by a portion of each of the plurality of plates; and controlling the spring mechanism to position the plurality of plates in one of the plurality of configurations.

10. The method according to claim 9, wherein the controlling step enables the stent to be positioned against a wall of the body lumen while maintaining flow through the body lumen.

11. The method according to claim 9, further providing a catheter in operable communication with the plate mechanism for guiding the plate mechanism within the body lumen.

12. The method according to claim 9, providing at least one control knob for controlling the spring mechanism.

13. The method according to claim 12, further comprising providing locking structure to the at least one control knob for locking the at least one control knob in one of a plurality of positions.

14. The method according to claim 13, wherein movement of the at least one control knob from a first to a second position of the plurality of positions controls the tightness of the wire.

15. The method according to claim 13, wherein the at least one control knob comprises a syringe mechanism.

16. The method according to claim 15, wherein the syringe mechanism is in operative communication with the wire, and wherein motion of the syringe mechanism controls the tightness of the wire.

* * * * *